United States Patent [19]

Green

[11] Patent Number: 4,749,114
[45] Date of Patent: Jun. 7, 1988

[54] PURSE STRING APPLICATOR AND METHOD OF AFFIXING A PURSE STRING

[75] Inventor: David T. Green, Norwalk, Conn.

[73] Assignee: United States Surgical Corporation, Norwalk, Conn.

[21] Appl. No.: 928,988

[22] Filed: Nov. 10, 1986

[51] Int. Cl.$^4$ ............................................... B25C 5/06
[52] U.S. Cl. ................................. 227/19; 128/334 R
[58] Field of Search ........................... 227/19, DIG. 1; 128/334 R, 334 C, 346

[56] References Cited

U.S. PATENT DOCUMENTS

| | | | |
|---|---|---|---|
| 3,683,925 | 8/1972 | Frankel | 128/334 C |
| 4,198,982 | 4/1980 | Fortner et al. | 227/DIG. 1 X |
| 4,345,600 | 8/1982 | Rothfuss | 128/334 R |
| 4,592,354 | 6/1986 | Rothfuss | 227/19 |

Primary Examiner—E. R. Kazenske
Assistant Examiner—James L. Wolfe
Attorney, Agent, or Firm—Kenyon & Kenyon

[57] ABSTRACT

The applicator is provided with a pair of handles and an anvil carrier against which rows of staples can be ejected. The applicator includes support elements for supporting the stapler cartridges and pushers for pushing the staples from the cartridges when the handles are squeezed together. Each cartridge carries a section of a string in the plane of the staples so that after ejection of the staples, the string is fixed about the periphery of an aperture in the tissue for use as a purse string in an end-to-end anastomosis procedure.

23 Claims, 4 Drawing Sheets

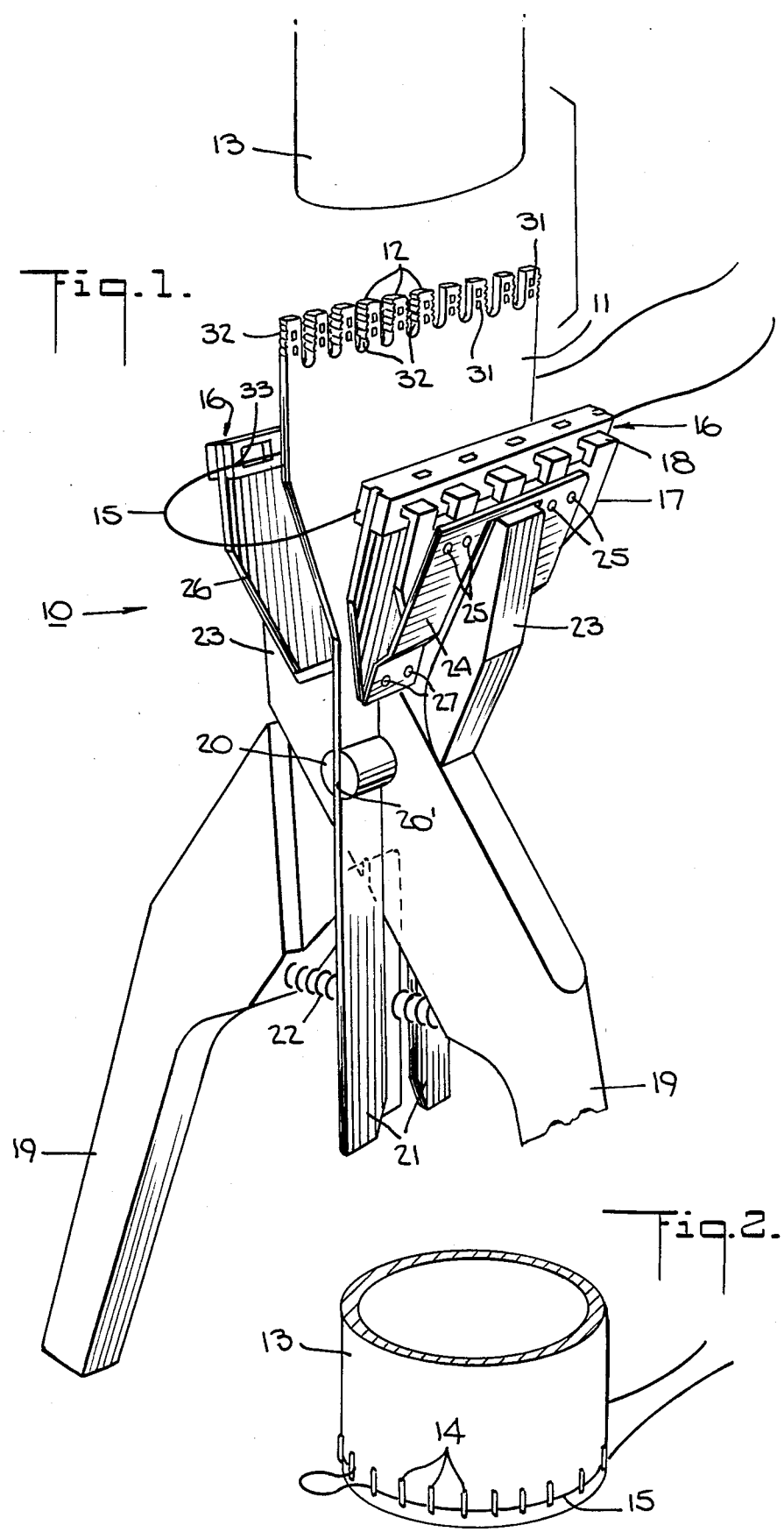

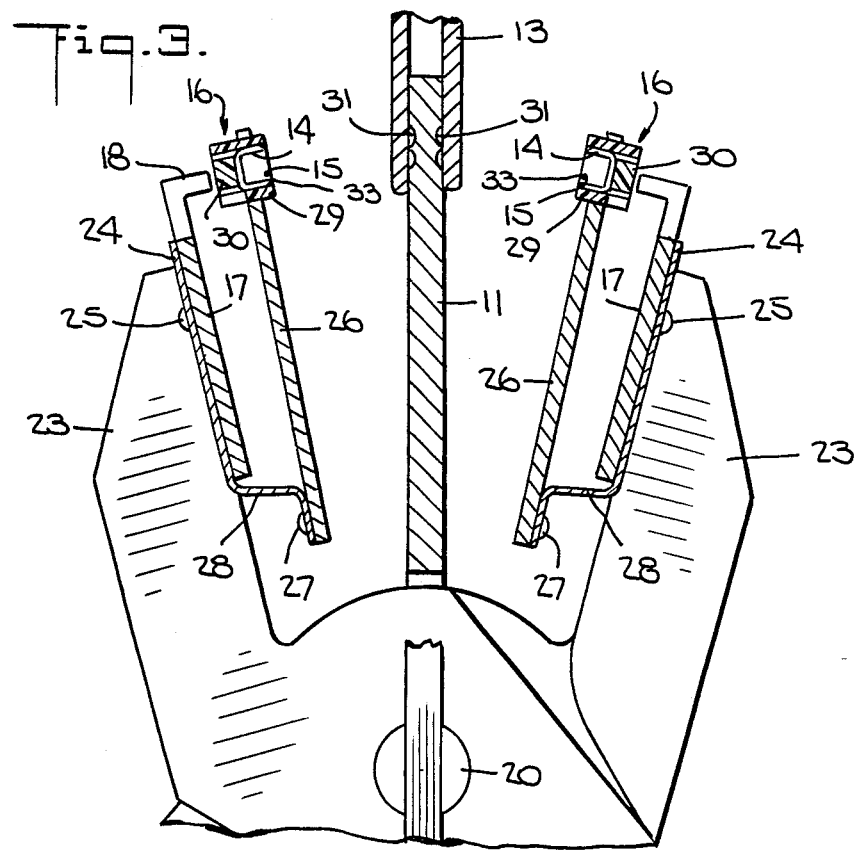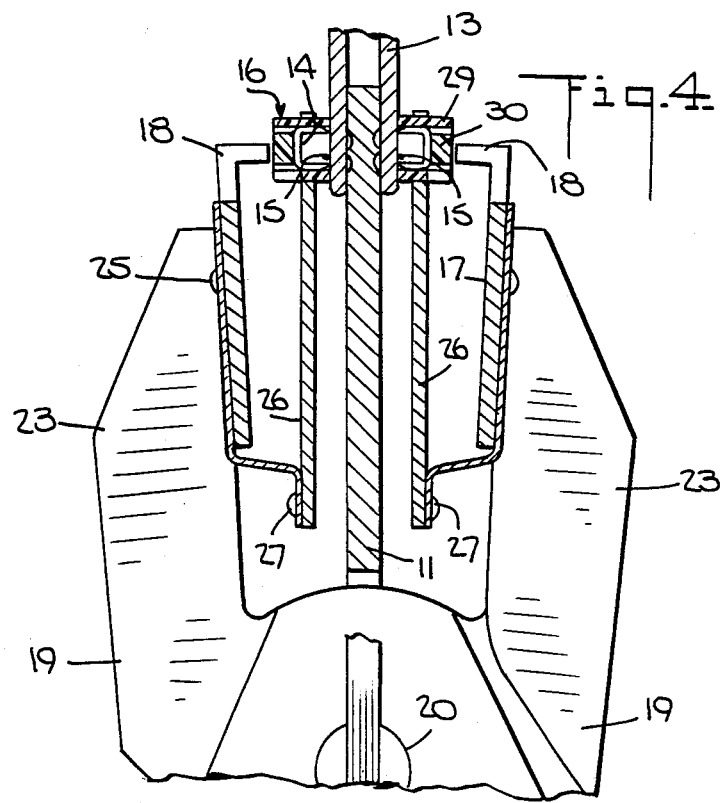

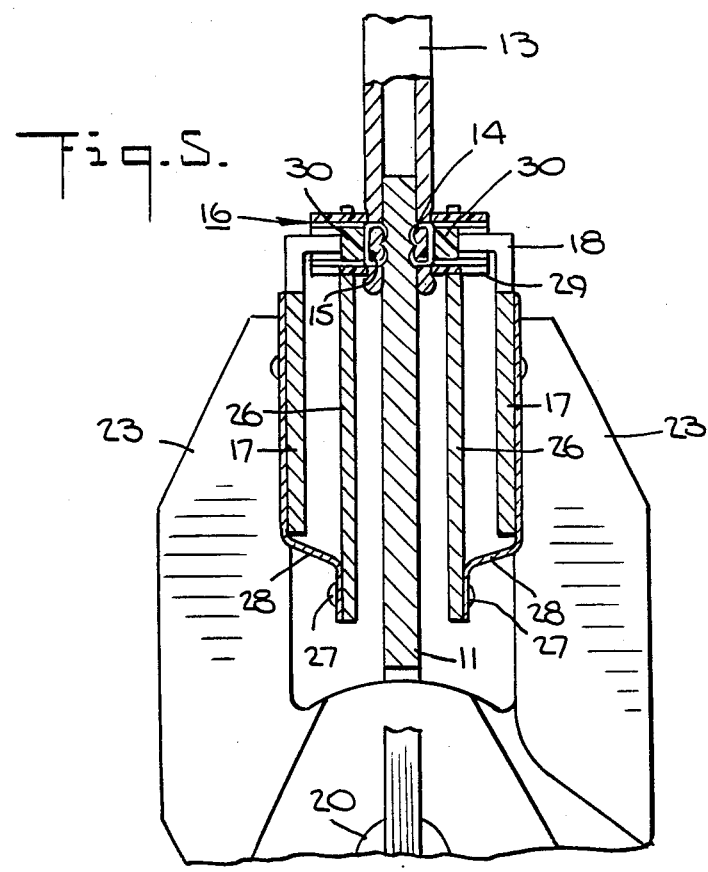
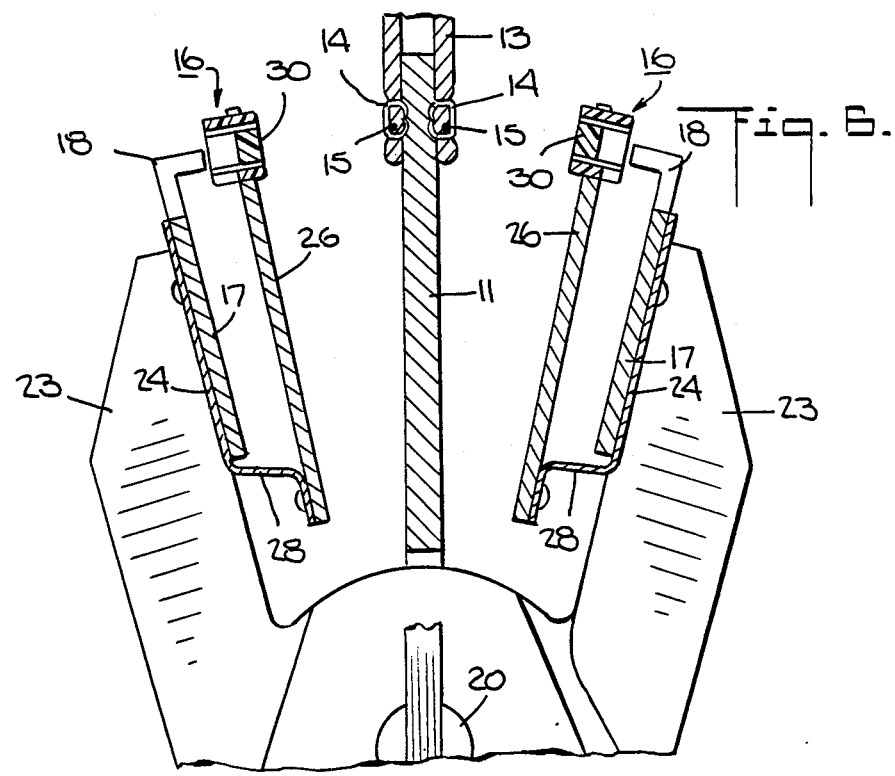

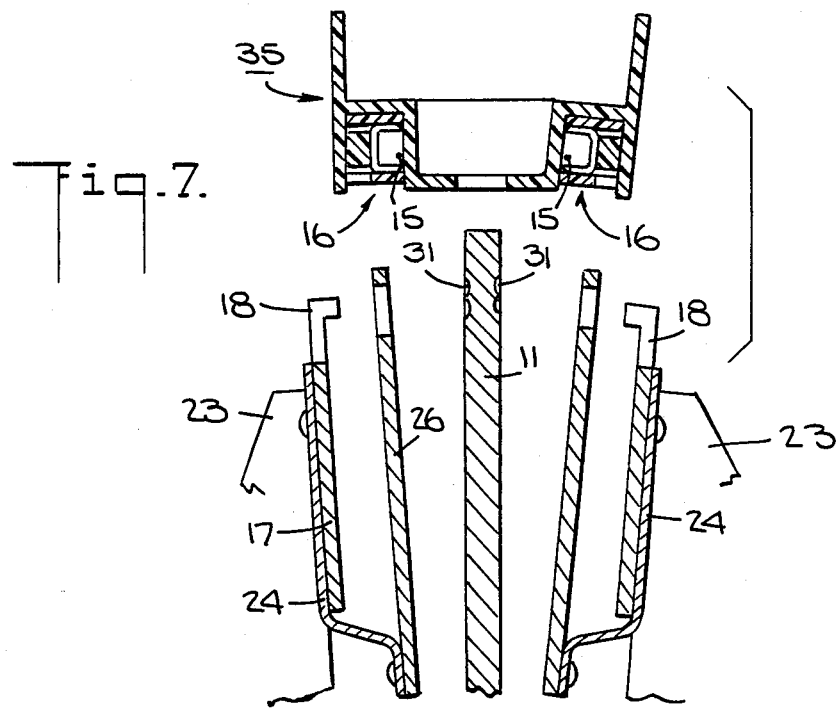
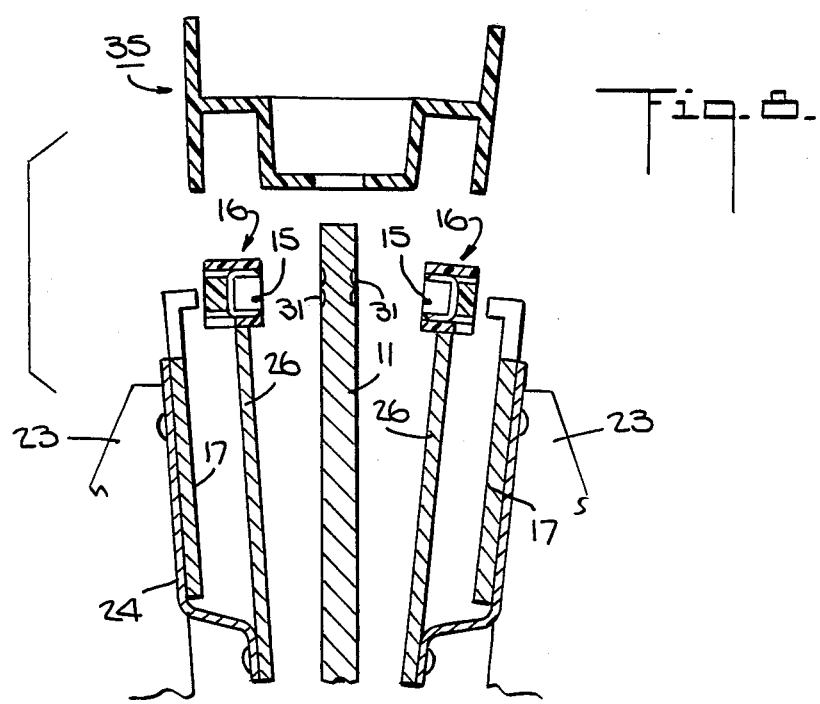

PURSE STRING APPLICATOR AND METHOD OF AFFIXING A PURSE STRING

This invention relates to a purse string applicator and to a method of affixing a purse string to a vessel.

Heretofore, a need has arisen in an end-to-end anastomosis procedure wherein two tubes or tubular tissue sections are joined end-to-end to provide each tube or section with a so-called purse string. Such a string is used to draw the end of a tube or tubular section inwardly so as to permit joining to another tube or tubular section using a suitable instrument such as a stapling instrument which is capable of ejecting one or more circular rows of staples to join the tubes or sections together. Various instruments have been used to perform this technique and need not be further described.

In the past, instruments have been provided to permit a surgeon to thread a string into a severed vessel or tube in order to provide the desired purse string arrangement. For example, one known instrument which is marketed by United States Surgical Corporation under the designation ASP50 is in the form of a scissor-like structure having a pair of jaw-like bars at the ends. Each bar is provided with a plurality of "teeth" as well as stops so as to clamp a tubular vessel therebetween and to deform the thus flattened vessel into an undulating pattern. In addition, each bar contains an elongated slot which passes through the teeth of the bar to threading in of a string. When in use, after the jaw-like bars of the instrument have clamped and deformed a vessel into a wave-like configuration, a needle with a trailing thread is then passed through one slot in one bar and, thus through the undulations of the vessel. After passing through one bar, the needle and thread are threaded through the second bar. Thereafter, the vessel is released from the instrument with a string then threaded through and around the periphery of the vessel. The vessel can then be secured to a second similarly prepared vessel using an anastomosis instrument as is known.

The use of the above type of purse string applicator is generally satisfactory. However, in some cases, the time required to affix a purse string to a vessel may be too long. Further, the need to manually thread a needle and thread through the jaw-like bars of an applicator can be cumbersome for some surgeons and time consuming.

Accordingly, it is an object of the invention to provide an improved purse string applicator which does no require manual threading of a string into a tubular vessel.

It is another object of the invention to provide an instrument which can automatically attach a purse string to a vessel.

It is another object of the invention to reduce the time require within which to attach a purse string to a vessel.

Briefly, the invention provides a purse string applicator which includes an anvil carrier having anvils for receiving an apertured section of tissue and means for applying at least one row of staples to the tissue on the carrier with a string extending across and slidably between the row of staples and the tissue.

The applicator is constructed so that one or more rows of staples can be driven into the tissue from the outside along with a string so that the string is connected to the tissue and lies around the outside periphery of the tissue. The attachment of the string to the tissue via the staples is such that the string may be slid relative to the staples and the tissue when the need arises to draw in the tissue, for example, for an anastomosis procedure.

The means for applying the staples includes a pair of cartridges which are disposed on opposite sides of the anvil carrier with each cartridge having a row of staples therein and with the string extending across and in the plane of each row of staples. In addition, the means includes a pair of pushers each of which has a plurality of pusher fingers aligned with a row of staples in order to expel the staples against the anvils of the carrier and through a wall of the tissue. In this regard, each cartridge is constructed with a common pusher bar which can be pushed by the pusher fingers in order to expel the staples. Alternatively, each cartridge may be made of individual segments, each of which houses two or more staples and a common pusher bar which can be actuated by a respective pusher finger of a pusher.

The use of individual cartridges permits the applicator to be used for differently sized tissue. However, for simplicity, one size cartridge would be used for different sized tissues. In this case, all of the staples would be ejected and clinched simultaneously. The staples which do not pierce through any tissue would, however, remain fixed on the string and would eventually be eliminated with the string.

The applicator may use a pair of handles which are articulated to the anvil carrier for movement relative to each other in order to eject the staples from the cartridges. In this case, each handle mounts a respective pusher thereon so that the closing force on the handles can be used to eject the staples.

The applicator is also provided with a pair of support elements on which the staple cartridges can be mounted, for example in a removable manner. Each of the support elements is further mounted via a spring support so as to permit movement of a pusher relative to the support element for expelling a row of staples in a cartridge mounted on each support element. In this way, the applicator serves not only to position the cartridges adjacent to a vessel which has been placed on the anvil carrier but also serves to eject the staples into the vessel after being positioned.

The invention also provides a method of affixing a purse string to an apertured section of tissue. This method includes the steps of positioning a plurality of staples about the periphery of the apertured tissue, positioning a string across and within the plane of the staples and driving the staples through a wall of the tissue to slidably dispose the string between the staples and the outer periphery of the tissue. The method can be performed with the periphery of the tissue flattened and with the staples driven from opposite sides of the flattened tissue. These and other objects and advantages of the invention will become more apparent from the following detailed description taken in conjunction with the accompany drawings wherein:

FIG. 1 illustrates a perspective view of a purse string applicator constructed in accordance with the invention;

FIG. 2 illustrates a tubular vessel having a purse string attached thereon in accordance with the invention;

FIG. 3 illustrates an initial stage of operation of the applicator of FIG. 1 with a tubular vessel mounted on the anvil carrier;

FIG. 4 illustrates a position of the applicator with the staple containing cartridges initially positioned adjacent a vessel;

FIG. 5 illustrates a view of the applicator after ejection of the staples from the cartridges;

FIG. 6 illustrates a view of the applicator after application of the purse string;

FIG. 7 illustrates an exploded view of a cartridge holder for mounting a pair of removable cartridges on the applicator in accordance with the invention; and FIG. 8 illustrates an exploded view of the cartridge holder after mounting of the cartridges on the applicator.

Referring to FIG. 1, the purse string applicator 10 includes an anvil carrier 11 having a row of anvils 12 at an upper end, as viewed, for receiving an apertured section of tissue such as a tubular vessel 13 in a flattened sleeve-like condition as well as means for applying staples 14 (not shown) to the vessel 13 with a string 15 extending across and slidably between the row of staples 14 and the vessel 13 (FIG. 2). As indicated, the means for applying the staples 14 includes a pair of cartridges 16 which are disposed on opposite sides of the anvil carrier 11 with each cartridge 16 having a row of staples 14 therein with the string 15 extending across and in the plane of each row of staples 14. In addition, the means includes a pair of digitated pushers 17 disposed to opposite sides of the anvil carrier 11. Each pusher 17 includes plurality of pusher fingers 18 which are aligned with a row of staples in order to expel each row of staples through a wall of the vessel 13 and against the anvils 12.

The applicator 10 also has a pair of handles 19 articulated for movement relative to each other. As indicated, each handle 19 is pivotally mounted about a common axis X defined by a fixed pivot 20. Further, the anvil carrier 11 is mounted to move longitudinally of the handles 19. To this end, the carrier 11 has a slot in the lower end, as viewed, to form two legs 21 each of which slides in a slot 20' of the pivot 20. A compression spring 22 is also provided between the handles 19 and passes through the slot in the anvil carrier 11 in order to bias the handles 19 outwardly of each other.

Each handle 19 is formed at the upper end with a jaw 23 which carries a pusher 17 as well as a spring support plate 24 sandwiched between the pusher 17 and jaw 23. Suitable rivets 25, or the like, are provided to secure the spring support plate 24 to the back side of each pusher 17 while suitable means such as screws (not shown) are used to secure each plate 24 to a jaw 23.

Further, a support element 26 is secured, as by rivets 27, along the lower end of each spring support plate 24 and carries a staple containing cartridge 16 at the upper end in alignment with the pusher fingers 18. As shown in FIG. 3, each spring support plate 24 has a bend 28 at the lower end so as to mount the cartridge support plate 26 in a cantilever manner in front of a pusher 17. Each cartridge support element 26 is suitably constructed to hold a cartridge 16 in permanent manner or in a detachable manner.

Referring to FIG. 3, each cartridge 16 has a common housing 29 in which a plurality of U-shaped staples 14 are mounted along with a common pusher bar 30. Suitable apertures are also provided to receive the pusher fingers 18 for moving the pusher bar 30 towards the staples 14.

Referring to FIG. 1, each anvil 12 is provided with grooves or buckets 31 on each of two opposite sides to receive the free ends of a staple 14 so as to deform the staple 14 into a B shape. In addition, the remaining sides of each anvil 12 is provided with a serration 32 in order to firmly grip a vessel 13 thereon.

Each cartridge 16 also includes a groove 33 which extends along and through the face of the cartridge 16 facing the anvil carrier 11. As indicated in FIG. 3, the string 15 is disposed in each groove 33 and is in the plane of the row of staples 14 in the cartridge 16.

The two support elements 26 and the cartridges 16 serve to define a means for positioning a row of staples 14 opposite each of the two opposite sides of the anvils 12 with the string 15 extending along and within the plane of each row of staples 14. The pair of digitated pushers 17 and the spring supports 24 serve to define a means for moving each row of staples 14 through the wall of a vessel 13 and against a respective side of the anvils 12 with the purse string 15 slidably disposed between each row of staples 14 and the vessel 13.

In order to use the applicator 10, the cartridges 16 are first put in place. Next, if the string 15 has not been pre-applied i.e., supplied with the cartridges 16, the string 15 is put in place, for example by an attending nurse.

Thereafter, the anvil carrier 11 is slid outwardly and the vessel 13 which is to be provided with a purse string is slid over the digitated end of the anvil carrier 11 so as to be spaced about the anvils 12, as indicated in FIG. 3.

Next, as indicated in FIG. 4, the anvil carrier 11 is retracted into a position between the handles 19 of the applicator and the cartridges 16. The handles 19 are then squeezed together to move the cartridges 16 against the vessel 13. Only a slight amount of force is required for this step.

Thereafter, the handles 19 are further squeezed together so as to move the pushers 17, as indicated in FIG. 5, towards each other. During this time, the pusher fingers 18 move into the respective cartridges 16 to cause the respective pusher bars 30 to eject the staples 14 against the anvils 12. This causes deformation of the U-shaped staples 14 into a B-shape while at the same time trapping the string 15 about periphery of the flattened vessel 13. Of note, the amount of deformation of the vessel wall is such that the string 15 remains slidable between the staples 14 and the vessel 13.

Next, the handles 19 are released so that the cartridges 16 are moved away from the vessel 13, as indicated in FIG. 6, leaving the staples 14 and string 15 in place. The flattened vessel 13 may then be slid off the anvil carrier 11.

After sliding off the anvil 12, the vessel 13 may take up a position as shown in FIG. 2. At this time, the loose loop of the string 15 which is shown to the left of FIG. 2 may be drawn in by pulling on the two free ends of the string 15. The string 15 is otherwise in position to function as a purse string in an end-to-end anastomosis procedure.

Referring to FIGS. 7 and 8, wherein like reference characters indicate like parts as above, a common cartridge holder 35 may be used to mount the cartridges 16 on the support elements 26. In this regard, where the applicator 10 is constructed for multiple use, the support elements 26 are constructed to removably mount the cartridges 16 thereon. In addition, the cartridges 16 are adapted to be mated to each support element 26, for example in a snap-fit manner. When the applicator 10 is in an open condition, the cartridge holder 35 is passed downwardly over the anvil carrier 11 and the two cartridges 16 are snapped in place on top of the support elements 26. Thereafter, the cartridge holder 35 can be lifted while the cartridges 16 are firmly in place on the support elements 26.

The applicator 10 can be readily manipulated by a surgeon using one hand after the stapled cartridges have been mounted in place, for example by a nurse. To this end, the surgeon need only insert the anvil carrier 11 into a vessel 13 to flatten the vessel across the anvils 12. Thereafter, upon squeezing the handles 19 together, two rows of staples 14 can be affixed to the periphery of the vessel with a purse string 15 held between the staples 14 and the vessel 13 as shown in FIG. 2. After release of the handles 19, the anvil carrier 11 can be slipped out of the vessel 13.

The string which is to be used with the applicator cartridges may be pre-applied to the cartridges so that the cartridges and string can be mounted as a unit applicator.

The purse string applicator 10 may be used to affix a purse string to different sized vessels. For example, for a smaller sized tubular vessel than that shown in FIG. 1, the vessel may be placed over only some of the anvils 12. Upon actuation of the handles 19 a string would be applied to the vessel while the staples which do not pierce the vessel would remain on the string for subsequent elimination with the string.

While the applicator 10 has been shown in use with a tubular vessel, the applicator may also be used to apply a purse string about an aperture in any apertured section of tissue.

The invention thus providies an applicator which can quickly and automatically affix a purse string to an apertured section of tissue.

The invention also provides a purse string applicator which can be used in a relatively simple time-saving manner.

What is claimed is:

1. A purse string applicator comprising
an anvil carrier having anvils for receiving an apertured section of tissue; and
means for applying at least one row of staples and a string to the section of tissue on said carrier with said string extending across and slidably between the row of staples and the tissue.

2. A purse string applicator as set forth in claim 1 wherein said means includes a pair of cartridges disposed on opposite sides of said anvil carrier, each cartridge having a row of staples therein with said string extending across and in the plane of each row of staples, and a pair of pushers, each pusher having a plurality of pusher fingers aligned with a row of staples to expel said row against said anvils and through the tissue.

3. A purse string application as set forth in claim 2 which further includes a pair of handles articulated for movement relative to each other, each said handle having a respective pusher mounted thereon.

4. A purse string applicator comprising
an anvil carrier having a row of spaced anvils for receiving an apertured section of tissue thereon in flattened condition;
first means for positioning a row of staples opposite each of two opposite sides of said anvils and a string extending along and within the plane of each said row of staples; and
second means for moving each row of staples through a wall of tissue and against a respective side of said anvils with the purse string slidably disposed between each row of staples and the tissue.

5. A purse string applicator as set forth in claim 4 wherein said first means includes a pair of support elements disposed on opposite sides of said anvil carrier and a pair of cartridges, each said cartridge being mounted on a respective support element with a row of staples therein.

6. A purse string applicator as set forth in claim 5 wherein each cartridge is removably mounted on said support element.

7. A purse string applicator as set forth in claim 5 wherein said second means includes a pair of digitated pushers and a pair of spring supports, each said pusher having a plurality of pusher fingers aligned with a respective row of staples and each spring support supporting a respective support element thereon to permit movement of a respective pusher towards a respective support element to expel a row of staples from a respective cartridge.

8. A purse string applicator as set forth in claim 7 which further comprise a pair of handles articulated for movement relative to each other, each said handle having a respective pusher mounted thereon.

9. A purse string applicator comprising
an anvil carrier having a row of spaced anvils for receiving an apertured section of tissue thereover;
a pair of support elements disposed on opposite sides of said anvil carrier;
a pair of cartridges, each said cartridge being mounted on a respective support element and having a row of staples therein;
a string extending across and carried on said cartridges within the plane of each said row of staples;
handle means for moving said support elements towards said anvil carrier to position said cartridges against the tissue on said anvils; and
second means for pushing each said row of staples from each respective cartridge through a wall of the tissue and against said anvils to deform and secure each staple to the tissue while retaining said string slidably between said staples and the tissue.

10. A purse string applicator as set forth in claim 9 wherein each anvil includes a groove on a side facing a respective cartridge for deforming a U-shaped staple thereon into a B shape.

11. A purse string applicator as set forth in claim 9 wherein each anvil has a pair of serrated side walls for selectively engaging apertured tissue.

12. A purse string applicator as set forth in claim 9 wherein each cartridge includes a plurality of spaced apart grooves in a surface facing said anvil carrier to receive said string therein.

13. A purse string applicator as set forth in claim 9 wherein said handle means includes a pair of handles secured to said support elements for moving said support elements towards and away from said anvil carrier.

14. A purse string applicator as set forth in claim 13 wherein said handles are pivotally mounted about a common axis in the plane of said anvil carrier.

15. A purse string applicator as set forth in claim 13 wherein said second means includes a pair of digitated pushers and a pair of spring supports, each said pusher being mounted on a respective handle with a plurality of pusher fingers aligned with a respective row of staples and each said spring support being mounted on a respective handle and supporting a respective support element thereon to permit movement of a respective support element in response to closing of said handles together.

16. A purse string applicator as set forth in claim 15 wherein each cartridge includes a pusher bar aligned with a row of staples and with said pusher fingers of a respective pusher.

17. A purse string applicator as set forth in claim 9 wherein said second means includes a pair of digitated pushers and a pair of spring supports, each said pusher being mounted on said handle means with a plurality of pusher fingers aligned with a respective row of staples and each said spring support being mounted on said handle means and supporting a respective support element thereon to permit movement of a respective pusher towards a respective support element in response to closing of said handle means.

18. A purse string applicator as set forth in claim 9 wherein each cartridge is removably mounted on a respective support element.

19. A purse string applicator comprising
an anvil carrier having a row of spaced anvils for receiving a flatted apertured section of tissue, each said anvil having a staple deforming groove in each of two opposite sides thereof;
a pair of support elements disposed on opposite sides of said anvil carrier for supporting staple-containing cartridges thereon;
a pair of pushers disposed on opposite sides of said anvil carrier for expelling staples from cartridges on said support elements, each said pusher being spaced from a cartridge support element; and
a pair of handles articulated to said anvil carrier and said pushers for moving said pushers towards each other and towards said support elements and said anvil carrier in response to closing of said handles towards each other to expel staples from cartridges on said support elements against said anvils and through a wall of the tissue on said anvils.

20. A method of affixing a purse string to an apertured section of tissue comprising the steps of
positioning a plurality of staples about the periphery of the apertured section of tissue;
positioning a string across and within the plane of the staples; and
driving the staples through a wall of the tissue to slidably dispose the string between the staples and the tissue.

21. A method as set forth in claim 20 which further comprises the step of flattening the section of tissue and thereafter driving the staples from opposite sides of the flattened tissue.

22. A method as set forth in claim 20 which further comprises the steps of inserting a row of anvils into an aperture of a section of tissue to flatten the tissue prior to driving of the staples into the walls of the tissue.

23. A purse string applicator comprising
an anvil carrier having anvils for receiving an apertured section of tissue thereon in flattened condition;
means for applying at least one row of staples to the section of tissue on said anvil carrier, said means including at least one cartridge having a row of staples therein and a groove in a face thereof having a string extending across and in the plane of said row of staples.

* * * * *

UNITED STATES PATENT AND TRADEMARK OFFICE
CERTIFICATE OF CORRECTION

PATENT NO. : 4,749,114
DATED : June 7, 1988
INVENTOR(S) : DAVID T. GREEN

It is certified that error appears in the above-identified patent and that said Letters Patent is hereby corrected as shown below:

```
Column 1, line 29  "to threading" should be -to permit threading-
Column 1, line 49  "no" should be -not-
Column 1, line 56  "require" should be -required-
Column 2, line 59  "accompany" should be -accompanying-
Column 4, line 42  "about" should be -about the-
Column 5, line 18  "unit appli-cator" should be -unit on the
       applicator-
Column 5, line 54  "application" should be -applicator-
Column 6, line 22  "comprise" should be -comprises-
Column 7, line 22  "flatted" should be -flattened-
```

Signed and Sealed this

First Day of November, 1988

Attest:

DONALD J. QUIGG

*Attesting Officer*    *Commissioner of Patents and Trademarks*